United States Patent
Roach et al.

(10) Patent No.: US 7,352,176 B1
(45) Date of Patent: Apr. 1, 2008

(54) ROTATING CONCAVE EDDY CURRENT PROBE

(75) Inventors: Dennis P. Roach, Albuquerque, NM (US); Phil Walkington, Albuquerque, NM (US); Kirk A. Rackow, Albuquerque, NM (US); Ed Hohman, Albuquerque, NM (US)

(73) Assignee: Sandia Corporation, Albuquerque, NM (US)

( * ) Notice: Subject to any disclaimer, the term of this patent is extended or adjusted under 35 U.S.C. 154(b) by 14 days.

(21) Appl. No.: 11/502,085

(22) Filed: Aug. 10, 2006

(51) Int. Cl.
*G01N 27/82* (2006.01)
*G01R 33/12* (2006.01)

(52) U.S. Cl. .................. 324/240; 324/242; 324/228
(58) Field of Classification Search ............ 324/222, 324/228, 234–243
See application file for complete search history.

(56) References Cited

U.S. PATENT DOCUMENTS 5,399,968 A * 3/1995 Sheppard et al. ......... 324/242
6,014,024 A * 1/2000 Hockey et al. ............ 324/240
6,636,037 B1 * 10/2003 Ou-Yang ................. 324/240
7,301,335 B2 * 11/2007 Sun et al. ................ 324/240

FOREIGN PATENT DOCUMENTS

| GB | 2273782 | * | 6/1994 |
| JP | 411148876 | * | 6/1999 |
| WO | WO 2007/015705 A3 | | 2/2000 |

* cited by examiner

*Primary Examiner*—Reena Aurora
*Assistant Examiner*—Kenneth J Whittington
(74) *Attorney, Agent, or Firm*—Robert D. Watson

(57) ABSTRACT

A rotating concave eddy current probe for detecting fatigue cracks hidden from view underneath the head of a raised head fastener, such as a buttonhead-type rivet, used to join together structural skins, such as aluminum aircraft skins. The probe has a recessed concave dimple in its bottom surface that closely conforms to the shape of the raised head. The concave dimple holds the probe in good alignment on top of the rivet while the probe is rotated around the rivet's centerline. One or more magnetic coils are rigidly embedded within the probe's cylindrical body, which is made of a non-conducting material. This design overcomes the inspection impediment associated with widely varying conductivity in fastened joints.

20 Claims, 20 Drawing Sheets

SEC A-A

SEC A-A

SEC A-A

SEC A-A

SEC A-A

SEC A-A

SEC A-A

ROTATING CONCAVE EDDY CURRENT PROBE

FEDERALLY SPONSORED RESEARCH

The United States Government has rights in this invention pursuant to Department of Energy Contract No. DE-AC04-94AL85000 with Sandia Corporation.

CROSS-REFERENCE TO RELATED APPLICATIONS

This application has technical disclosure in common with U.S. application Ser. No. 11/664,665 filed Apr. 4, 2007.

BACKGROUND OF THE INVENTION

The present invention relates generally to methods and apparatus for using eddy current probes to non-destructively inspect and detect the presence of hidden fatigue cracks located underneath the head of a raised head fastener, such as raised head rivets used in joining aluminum skins of aircraft fuselages or bridge assembly girders.

Eddy Current (EC) inspection techniques use the principles of electromagnetic induction to identify or differentiate changes in structural conditions in conductive materials (e.g., metals). The presence of a crack is indicated by localized changes or perturbations in the flow of eddy currents in the conductive material (e.g., the aluminum skin of a helicopter) induced by the probe. Eddy current signals from EC probes are typically monitored using impedance-plane plots, which show the reactive (amplitude) component along the X-axis and resistive (phase) component along the Y-axis of an alternating electric current flowing through a coil of wire (i.e., magnetic test coil) housed inside of the EC probe. An alternating electric current flowing in the test coil creates an alternating magnetic field, which, when placed close enough to the conductive material, induces eddy currents to flow on the surface, and inside of, the conductive material. These induced eddy currents, in turn, generate their own magnetic field in a direction that opposes the applied magnetic field of the test coil. This opposing magnetic field changes the impedance of the test coil in a way that can be measured and displayed.

During EC inspection, the presence of a crack (or a change in the thickness of a part, change in conductivity, or other type of material discontinuity) causes localized perturbations in the flowing eddy currents induced by the probe. These perturbations show up as identifiable changes in the impedance-plane plot of the probe's test coil. EC instruments record these impedance changes, and display them in impedance-plane plots to aid in the flaw detection process.

Because eddy currents are created using an electromagnetic induction technique, the inspection method does not require direct electrical contact with the part being inspected. Also, the depth of penetration of eddy currents is inversely proportional to the product of three factors: magnetic permeability, electrical conductivity, and frequency of the alternating inducing currents. Therefore, eddy current tests are most sensitive to discontinuities on the surface underneath the coil, which makes them very effective for detecting fatigue cracks in the surface or near-surface region. Typically, high frequency eddy currents (HFEC) are generally considered to be 100 kHz and above and are used to detect near-surface flaws. Low frequency eddy currents (LFEC) are in the range of 100 Hz to 10 kHz and are used to penetrate deeper to detect flaws in the underlying structure. The thicker the structure, the lower the EC operating frequency that is required to inspect it. However, eddy currents flowing deeper in the material are weaker, and lag in phase, compared to the eddy currents near the surface or at an inner wall.

Eddy currents induced by an EC probe test coil are not uniformly distributed throughout the conductive skin. Rather, they are densest and strongest at the skin's surface immediately beneath the coil, and become progressively less dense (i.e., weaker) with increasing distance below the surface; as well as with increasing radial distance away from the coil's centerline. Thus, the inspection sensitivity (i.e., flaw detection sensitivity) is decreased by a "lift-off" effect as the gap between the probe head and the surface being inspected increases. This loss in sensitivity caused by the "lift-off" effect is significant when the EC probe is placed on top of the head of a raised head fastener, especially when trying to detect cracks in the structural member (i.e., skin) directly underneath the fastener's head (a typical raised head rivet can have a lift-off distance of as much as 1-3 mm). Hence, it is desirable to minimize the gap or "lift-off" distance between the EC probe's head and the skin being inspected.

Raised head fasteners (e.g., rivets) that are typically found in rotorcraft joints, aircraft fuselage frames, and many civilian structures (ships, bridges, towers, etc), interfere with the ability to place conventional eddy current probes close to the area of interest; i.e., the structural skin underneath the raised head fastener. It is difficult, if not impossible, with current technology (i.e., conventional EC probes) to generate sufficient eddy current fields under the fastener head for crack detection. Only when the fatigue crack has radially extended far enough outwards from underneath the fastener head (i.e., beyond the rivet head's outer radius, where it becomes visible), can conventional hand-held EC probes be successfully used.

When using any hand-held EC probes on raised head fasteners it is difficult to provide a consistent and stable orientation of the test coil with respect to the radial and circumferential position (relative to the rivet's centerline). It is also difficult to maintain the orientation of the coil's axis perpendicular to the rivet head's surface. Uncontrollable changes in the probes position and orientation as the probe is manually moved around on the rivet head and on the skin next to the rivet head, degrades the reliability and repeatability of the eddy current signal. These inspection impediments make crack detection around raised-head fasteners impossible to achieve with hand-held EC probes (such as pencil-type hand-held probes).

The small size of the test coil, and associated high operating frequencies, in conventional pencil-type EC probes limits the ability to detect cracks in the second, lower layer of skin. This is because lower EC frequencies are required to inspect the deeper regions of the structure, which, in turn, require larger diameter magnetic coils. Pencil-type EC probes also have difficulty detecting hidden, angled cracks underneath rivet heads (i.e., cracks that have not penetrated to the upper surface of the skin).

Other factors also affect the repeatability, reliability, and accuracy of crack detection using EC probes. In particular, a common problem involves the degree of electrical conductivity between the rivet fastener, the surface and the subsurface layers. The level of conductivity affects the eddy current signal by affecting the amount of current flowing through the rivet (as opposed to flowing through the skin). Many factors can affect the conductivity levels, e.g. (1) the type of fastener coating (e.g., an alodine coating on an aluminum rivet is less conductive than an anodized coating), and (2) the degree of coating removal from the fastener caused by fretting of the mating surfaces, which typically increases the joint conductivity; and (3) corrosion at the mating surfaces. Variations in the conductivity levels, and associated changes in eddy current response, can be a significant impediment to obtaining successful inspections. Small changes in the EC signal produced by cracks at rivet sites may be lost or overwhelmed by larger changes in the EC signal caused by joints with higher conductivity. Hence, a need exists for a way to eliminate uncertainties and "noise floor" problems caused by high conductivity joints.

FIG. 1A shows a schematic cross-section side view of a raised head fastener 2 (e.g., a solid rivet) holding together two structural skins, upper skin 7 and lower skin 8 (e.g., 2024 or 7075 aluminum alloy plates). Rivet 2 has a raised head 3, a cylindrical shank 4, and a deformed button (rivet upset region) 5 on the bottom. The rivet's shank 4 is located inside hole 6 in the structural skin 7 & 8. Fatigue crack 9 in upper skin 7 is shown lying underneath the fastener's head 3, completely hidden from view. In this example, crack 9 is illustrated as being located in the upper structural skin 7. However, such cracks can further extend into the lower skin 8, or, be located only in the lower skin, etc. Multiple fatigue cracks may emanate radially from hole 6 at different circumferential locations (e.g., at 0 and 180 degrees), depending on the stress state. These cracks may be thru-cracks (penetrating completely through a structural layer (i.e. skin) from front-to-back); or they may be sub-surface cracks that don't completely penetrate through the skin; and/or they may penetrate just one surface of a skin (e.g., an upper or a lower surface of a skin).

FIG. 1B shows a pair of conventional, hand-held eddy current probes 101 & 103 (e.g., "pencil" or "spot" probes). Probe 101 (with internal test coil 102) is manually placed directly on top of the rivet head 3, concentric with the rivet's centerline (i.e., axis of rotation). When probe 101 is held at this location, successful detection of hidden crack 9 can be difficult because of the large lift-off distance (i.e., the thickness, $t_{head}$, of rivet head 3), which reduces the amount of eddy current field 105 that can interact with crack 9. Alternatively, pencil probe 103 can be placed in direct contact with the upper/exterior surface of upper skin 7, outside of the rivet head's outer radius. However, even though the lift-off distance is essentially zero at this location, the concentrated eddy current field 106 is still located far away from crack 9 and, hence, can limit successful detection of crack 9 when hidden underneath rivet head 3.

In FIG. 1C, a conventional EC probe 101 is hand-held in contact with the rivet's head 3, inclined at an inclined angle, α, with respect to the rivet's centerline, and located at a radial distance, $R_{probe}$. As the inspector moves probe 101 by hand around the surface of the rivet, scanning and searching for cracks, the probe's radial position, $R_{probe}$, the inclination angle, α, and the gap/lift-off distance from the rivet head's surface, cannot be held perfectly steady/constant. These unavoidable changes in the probe's position, despite the best efforts of an experienced inspector, adds a large amount of undesirable "noise" to the probe's output signal that is actually in excess of the response generated by the fatigue crack itself. This eliminates the possibility of successful crack detection.

Because the use of hand-held EC probes is typically a labor-intensive, manual activity, a need exists for: 1) improved methods and probe designs that minimize the time needed to inspect a riveted structure, 2) a probe design that eliminates the position variations, and associated noise, to produce successful crack detection beneath raised-head fasteners, and 3) minimizing the need to go back and perform repeated inspections due to inconsistent or unreliable readings.

What is needed is an improved EC probe design that provides reliable, repeatable, accurate and consistent readings by eliminating the geometrical uncertainties associated with hand-held, manual positioning.

SUMMARY OF THE INVENTION

A rotating concave eddy current probe for detecting fatigue cracks hidden from view underneath the head of a raised head fastener, such as a buttonhead-type rivet, used to join together structural skins, such as aluminum aircraft skins. The probe has a recessed concave dimple in its bottom surface that closely conforms to the shape of the raised head. The concave dimple holds the probe in good alignment on top of the rivet while the probe is rotated around the rivet's centerline. One or more magnetic coils are rigidly embedded within the probe's cylindrical body, which is made of a non-conducting material. The rotating concave eddy current probe allows for crack detection by successfully addressing the needs listed above. In addition, it overcomes the inspection impediment associated with widely varying conductivity in fastened joints.

BRIEF DESCRIPTION OF THE DRAWINGS

The accompanying drawings, which are incorporated in and form part of the specification, illustrate various examples of the present invention and, together with the detailed description, serve to explain the principles of the invention.

DETAILED DESCRIPTION OF THE INVENTION

The term "rivet" is broadly defined herein to mean any type of "raised head" fastener. Thus, the term "rivet" includes screws, bolts, carriage bolts, stove bolts, solid rivets, blind rivets, multi-grip rivets, grooved rivets, tubular rivets, etc. The term "raised head" includes the following shapes: round head, universal head, brazier head, flat head, rounded head, domed head, pan head, pan head with chamfered outer edge, button head, truss head, cheese head, fillister head, socket head, countersunk with a rounded top, etc. These shapes are typically axisymmetric with respect to the fastener's central axis of revolution (centerline). Metals commonly used for raised head fasteners include steel, aluminum, titanium, brass, bronze, nickel alloys, etc. The term "non-conducting" means non-electrical conducting. The term "rotating eddy current probe means that the probe body is rotatable (i.e., can be rotated) during inspection around the central axis of the raised head rivet, either rotated by hand, or rotated by mechanical means, such as a motor, stepped-motor, or crank.

Figure 1A:
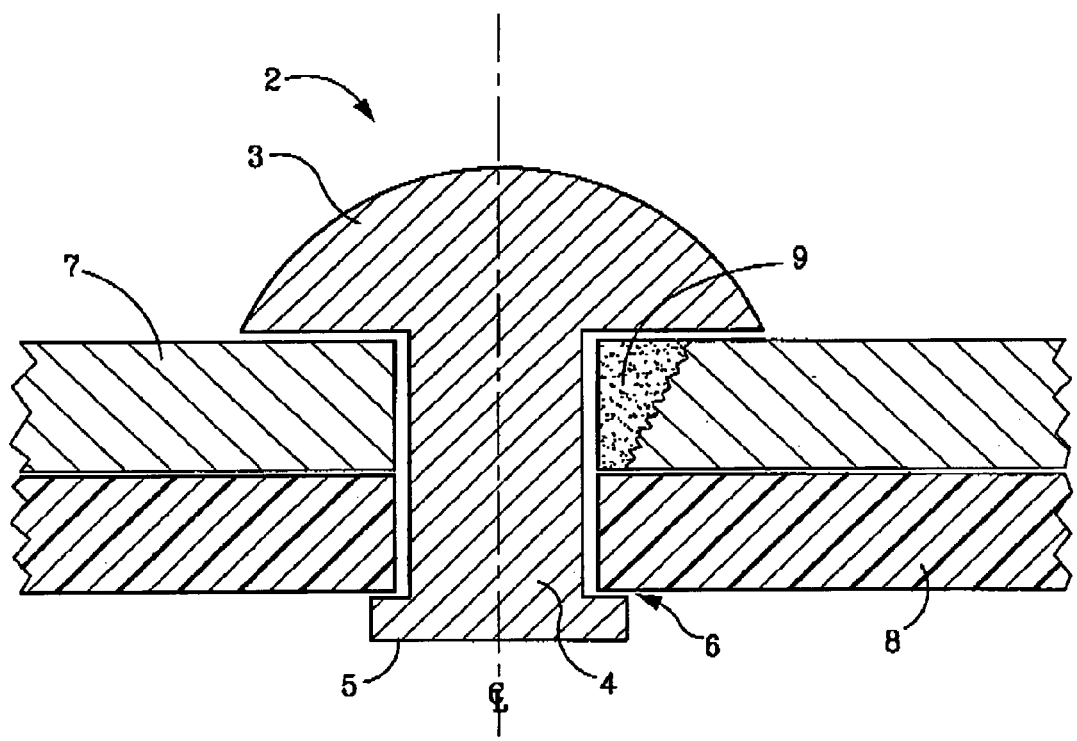
FIG. 1A shows a schematic cross-section side view of a raised head fastener (rivet) holding together two structural skins; where the upper skin has a fatigue crack underneath the fastener's head, hidden from view.
Figure 1B:
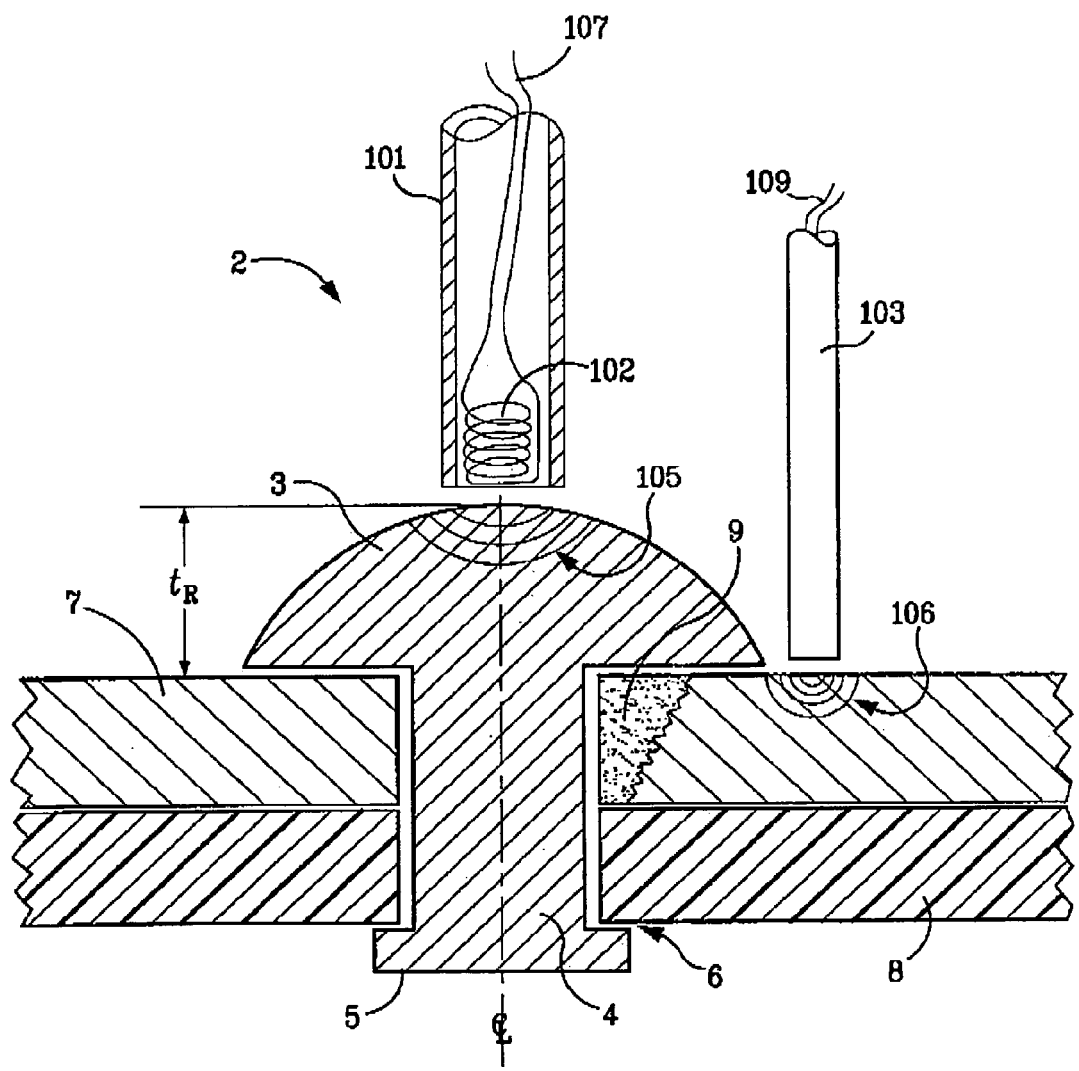
FIG. 1B shows a schematic cross-section side view of a pair of conventional EC probes deployed in the vicinity of a fatigue crack.
Figure 1C:
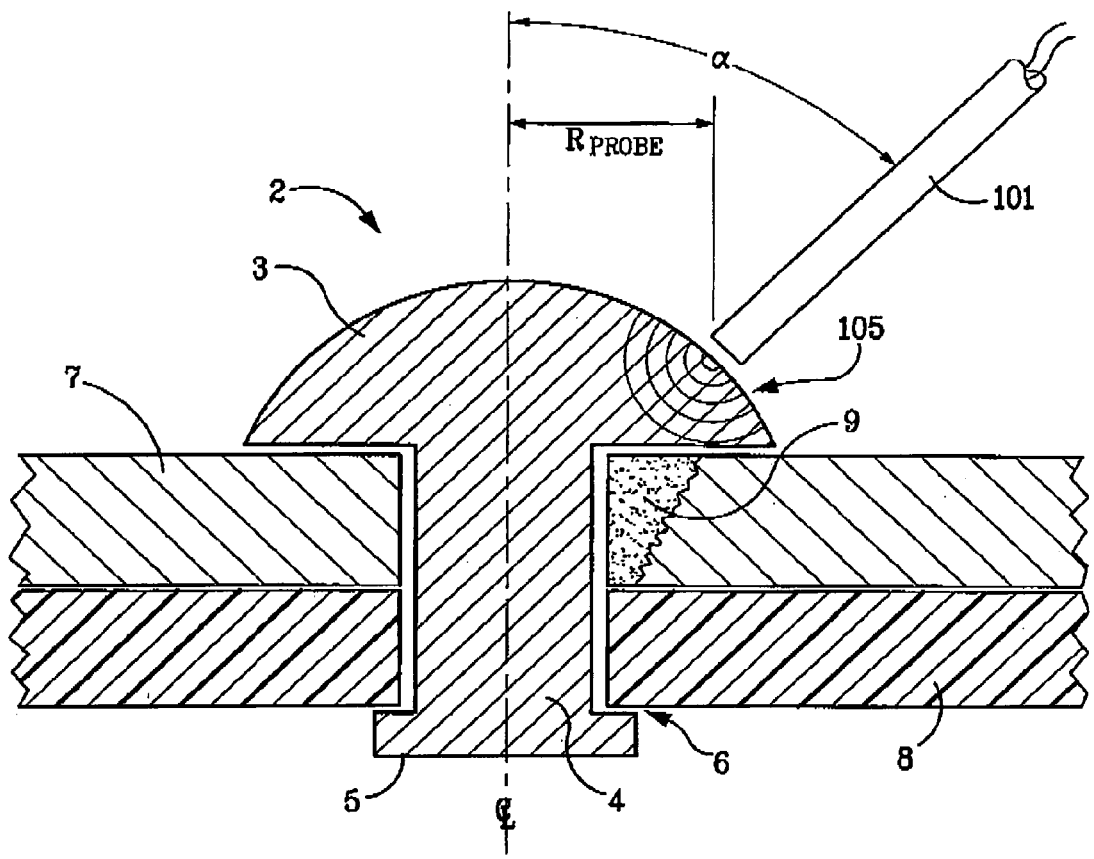
FIG. 1C shows an attempt to place a conventional EC probe in close proximity to a skin crack.
Figure 2A:
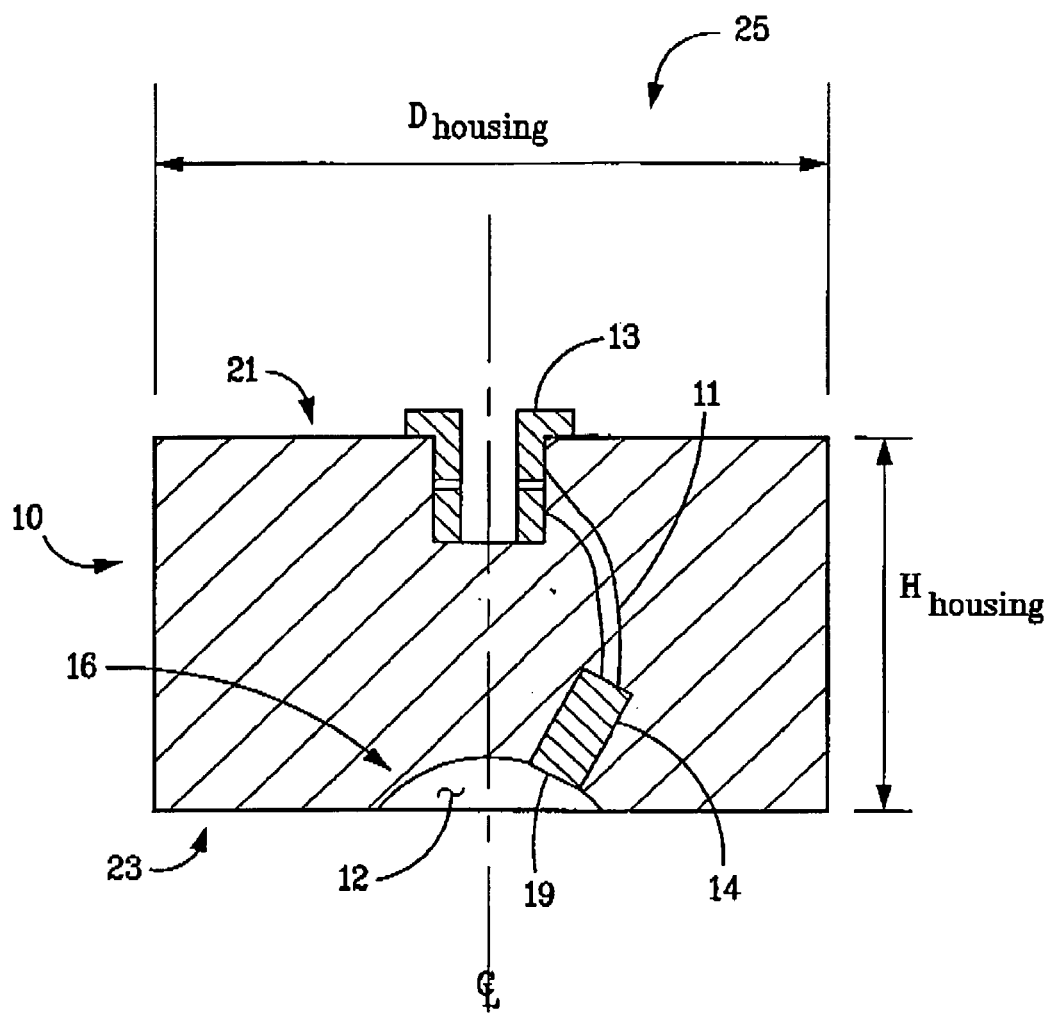
FIG. 2A shows a schematic cross-section side view of the first example of a rotating concave eddy current probe, according to the present invention.

FIG. 2A shows a schematic cross-section side view, Sec-AA, of a first example of a rotating concave eddy current probe, according to the present invention. Eddy current probe 25 comprises a right circular-cylindrical body/housing 10 made of a non-conducting material (such as plastic or ceramic), with a concave dimple 12 recessed into the probe's bottom surface 23. Body 10 has an outer diameter, $D_{housing}$, and a height, $H_{housing}$. The shape of the inner surface 16 of dimple 12 is axisymmetric about the probe's centerline, and is chosen to conform to, and to fit closely over, the head of a raised head fastener during inspection (see, for example, FIG. 3B). Magnetic test coil 14 is rigidly fixed/embedded inside of housing 10, with the lower end 19 of the coil being located flush with rotating concave inner surface 16. A coaxial electrical socket/connector/plug 13 is located on the upper surface 21 of probe 10, on the centerline. A pair of embedded electrical wires 11 connects socket 13 to coil 14.

Figure 2B:
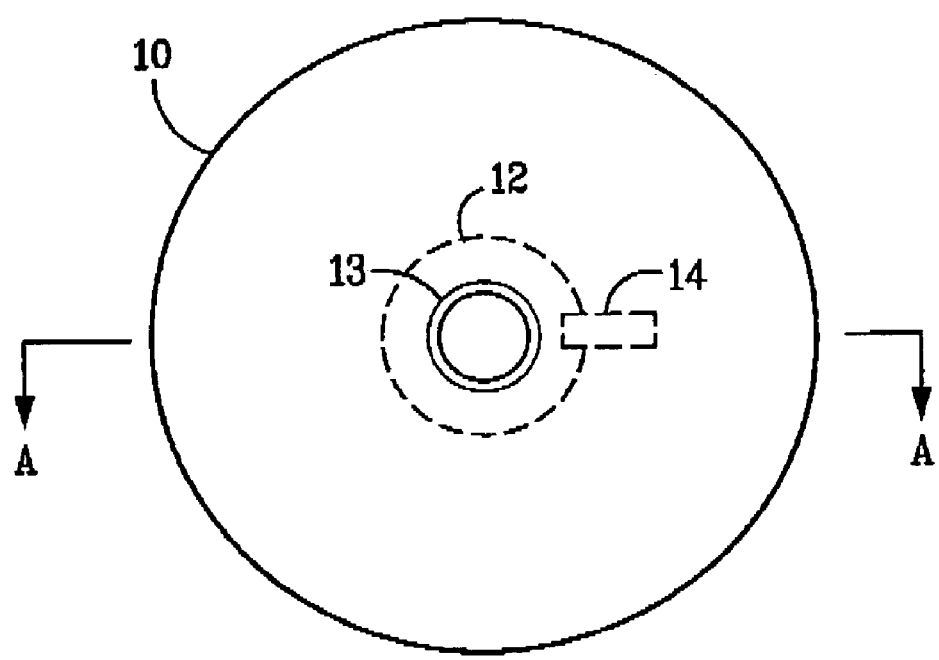
FIG. 2B shows a schematic top view of the probe of FIG. 2A.

FIG. 2B shows a schematic top view of the EC probe of FIG. 2A.

Figure 2C:
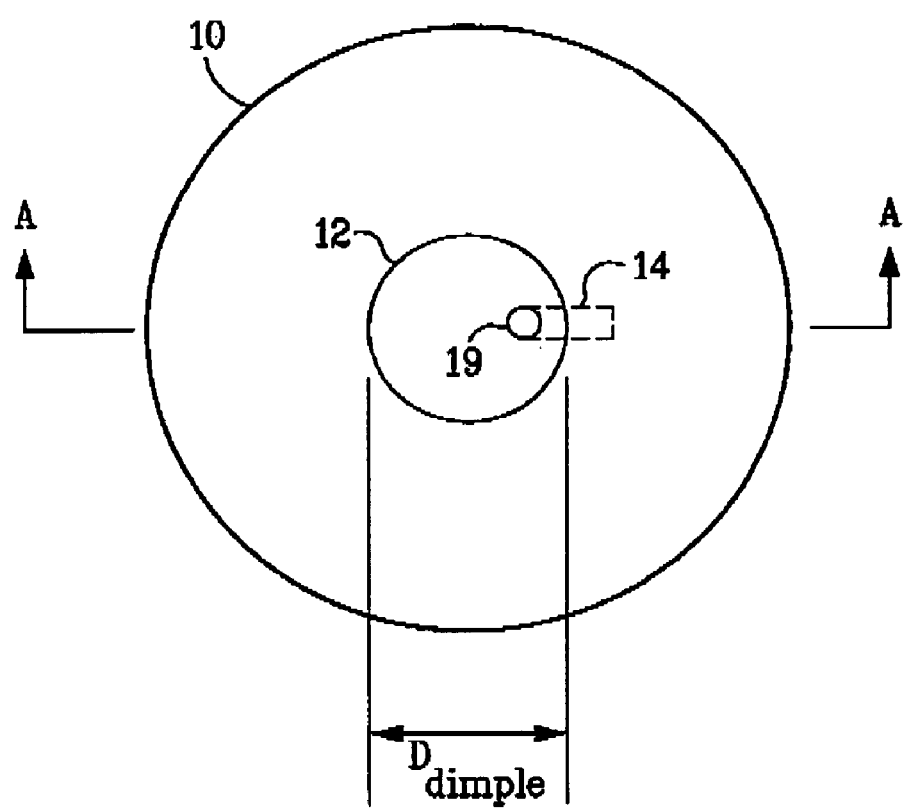
FIG. 2C shows a schematic bottom view of probe of FIG. 2A.

FIG. 2C shows a schematic bottom view of probe of FIG. 2A.

Figure 3A:
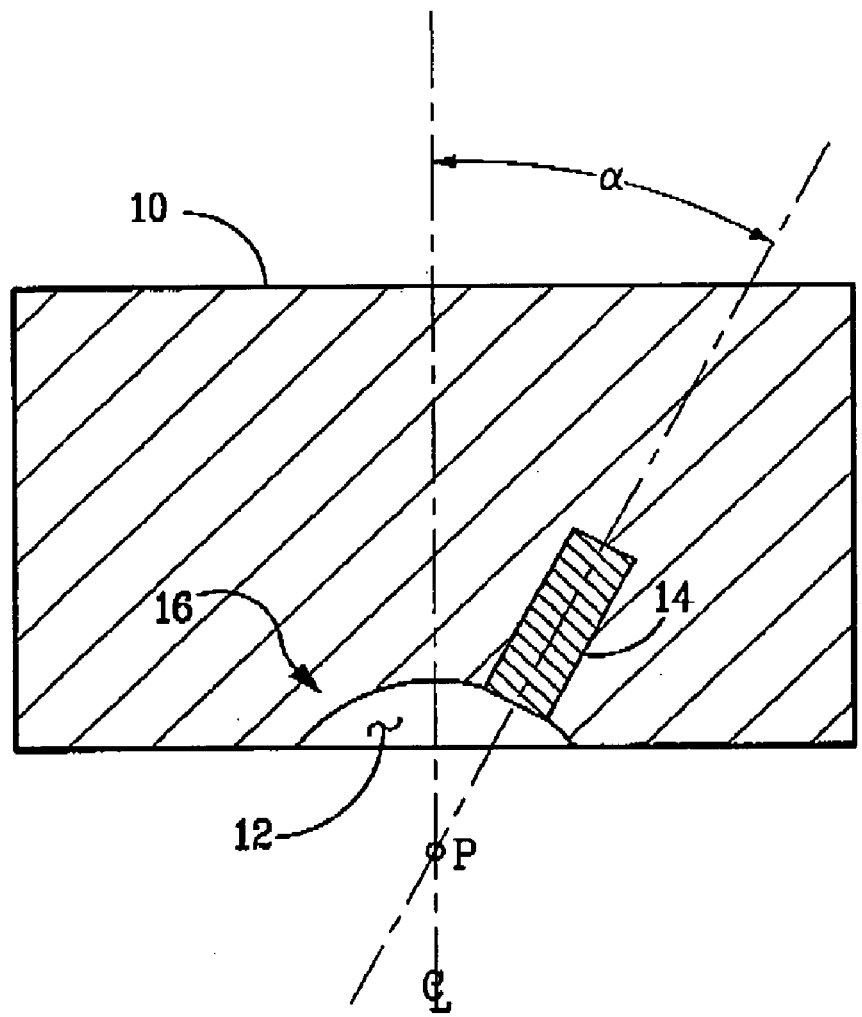
FIG. 3A shows a schematic cross-section side view of the rotating concave eddy current probe of FIG. 2A.

FIG. 3A shows a schematic cross-section side view of the rotating concave eddy current probe of FIG. 2A. The central axis of magnetic coil 14 intersects the probe's centerline at point "P", and forms an angle, $\alpha$, with respect to the centerline. The angle, $\alpha$, of coil 14 can be chosen to make the coil's axis perpendicular to the inner concave surface 16, as shown in FIG. 3-A. The angle, $\alpha$, can be from 0-90 degrees. Alternatively, the angle, $\alpha$, can be from 20-60 degrees. Alternatively, the angle, $\alpha$, can be from 30-50 degrees. Alternatively, the angle, $\alpha$, can be from 30-40 degrees. The angle, $\alpha$, can be chosen to maximize the EC signal, depending on the specific shape of rivet's head. The outside diameter of the probe body, $D_{housing}$, can be chosen to fit within the adjacent rivet lines, yet large enough to accommodate an eddy current coil of needed frequency. In one embodiment, the outside diameter of the probe body, $D_{housing}$, is greater than or equal to the outside diameter of the recessed concave dimple 12.

Figure 3B:
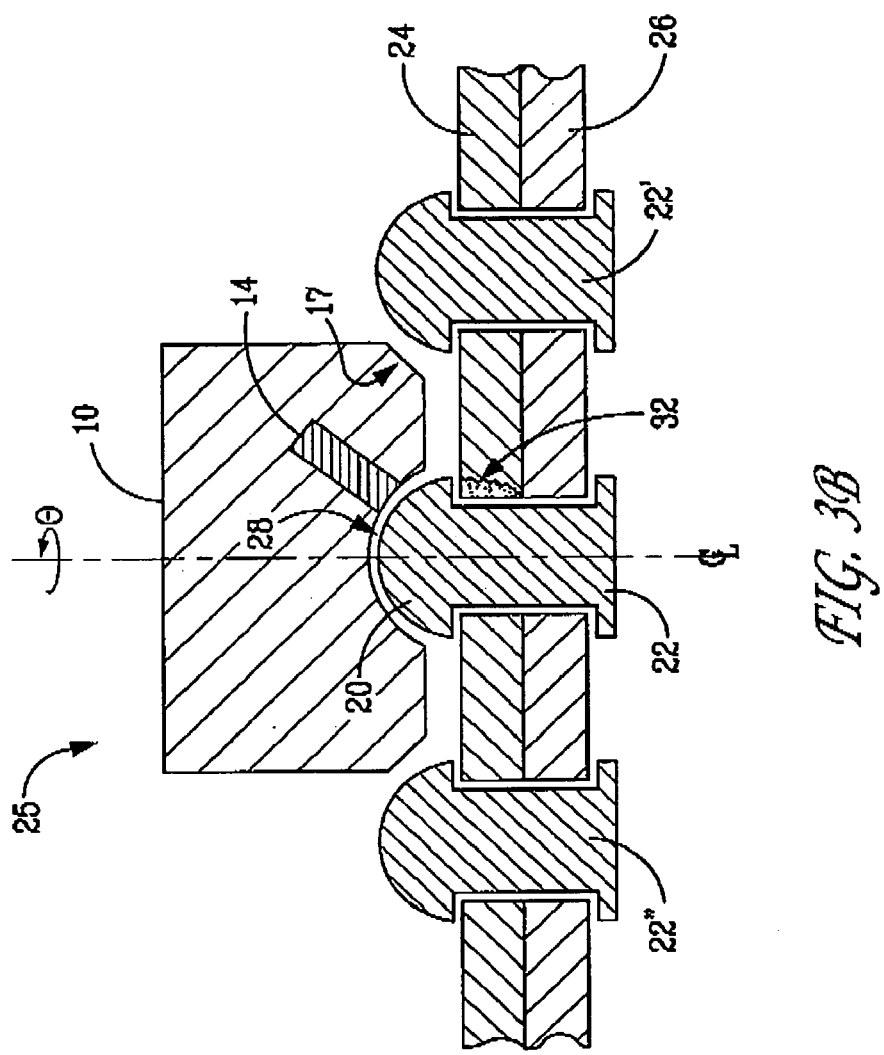
FIG. 3B shows a schematic cross-section side view of a rotating concave eddy current probe placed on top of raised head fastener, for inspecting underneath the head of the fastener.

FIG. 3B shows a schematic cross-section side view of a rotating concave eddy current probe, 25, placed on top of structural skin 24, and covering raised head fastener 22, for inspecting underneath the head 20 of fastener 22, according to the present invention. A small gap, 28, exists between the rivet's head 20 and the inner surface of the recessed dimple in probe body 10. The size of gap 28 in FIG. 3B is exaggerated for illustration. In practice, gap 28 can be less than 1 mm, and can be less than 0.1 mm. Gap 28 can be as small as 0.001 inches, depending on how well the concave dimple is manufactured. A close fit of the concave dimple to the raised head is desirable in order to minimize the lift-off distance (as discussed before), and to minimize any unnecessary side-to-side movement of the probe 25 during rotation of the probe body 10. In this sense, probe body 10 functions not only as a housing for rigidly holding test coils at a fixed orientation, but also as a fixture for accurately, reliably and repeatably aligning the coil(s) with respect to the rivet's centerline during inspection (which involves rotating the body 10 of probe 25 circumferentially around the rivet's centerline). Test coil 14 is oriented so as to be able to detect fatigue crack 32 hidden underneath head 20. Probe body 10 can have a chamfered bottom edge, 17, to permit the probe's outside diameter, $D_{housing}$, to be as large as possible, without hitting the adjacent rivets 22' and 22". The large diameter of housing 10 (i.e., compared to a conventional pencil-type EC probe) allows a much larger test coil 14 to be used (as compared to the EC probe example illustrated in FIG. 3A).

Figure 4A:
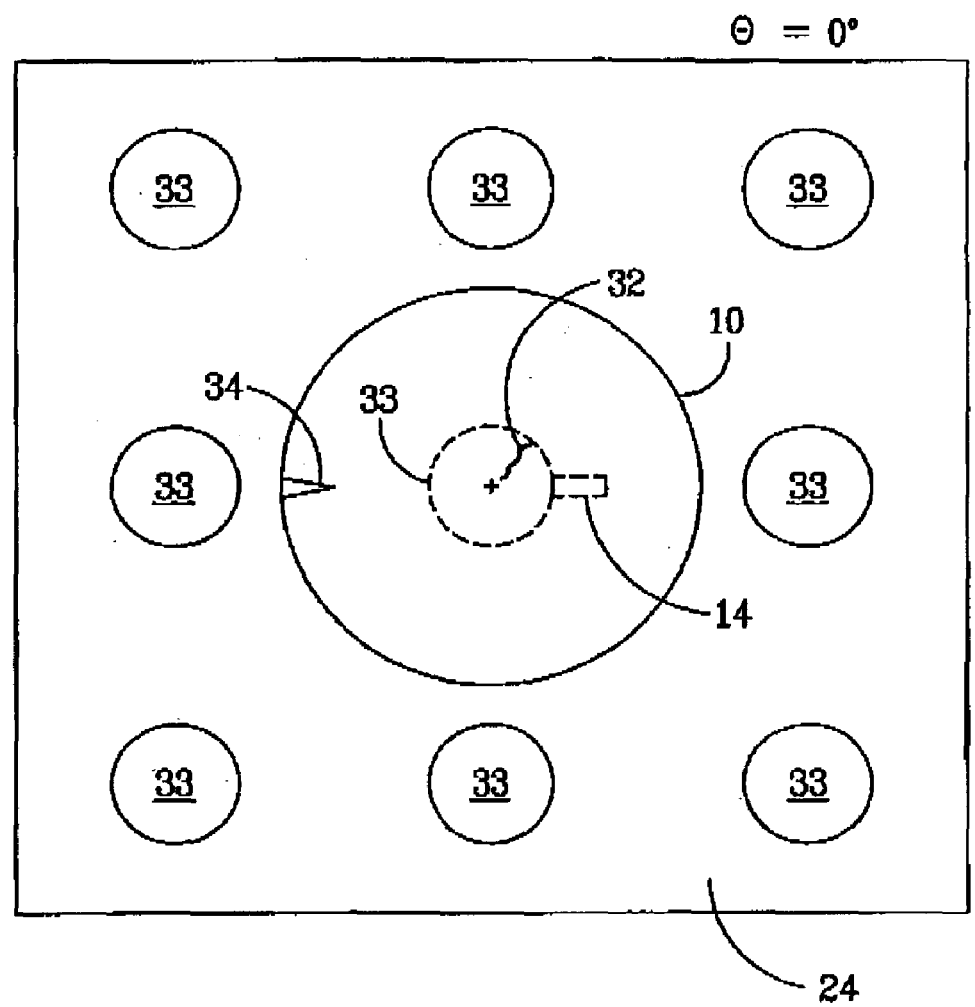
FIG. 4A shows a schematic top side view of a rotating concave eddy current probe placed on top of raised head fastener, with 0 degree circumferential (θ) rotation, according to the present invention.

FIG. 4A shows a schematic top-view of EC probe 10 placed on top of structural skin 24, and covering rivet 33, for inspecting underneath the rivet's head. FIG. 4A illustrates a 3×3 square array of rivets 33, with probe 10 being placed over the central rivet. Hidden crack 32 lies underneath the rivet's head. Probe 10 has a position mark 34, which indicates that the probe's circumferential position is at θ=0 degrees. Position mark 34 can be located on the top or side of probe body 10, or both, to aid the operator in knowing where the test coil 14 is located.

Figure 4B:
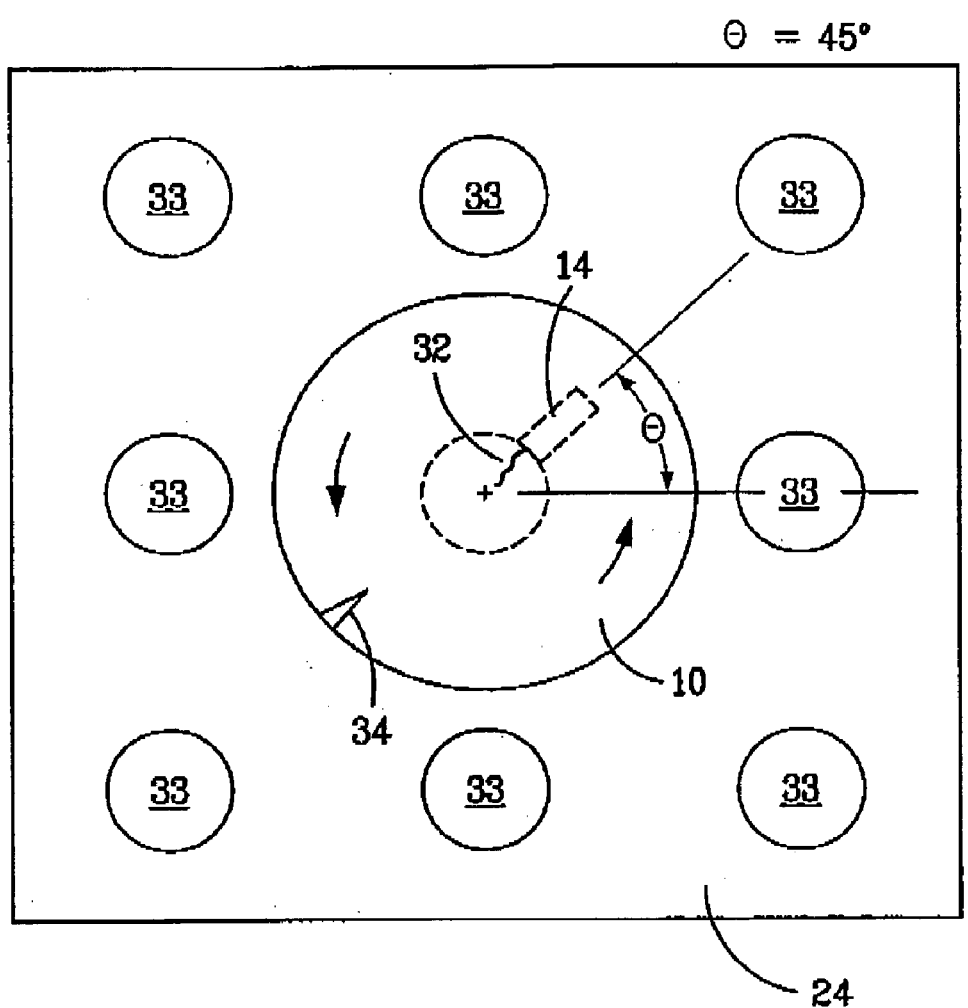
FIG. 4B shows a schematic top side view of a rotating concave eddy current probe placed on top of raised head fastener, with 45 degree circumferential (θ) rotation, according to the present invention.
Figure 4C:
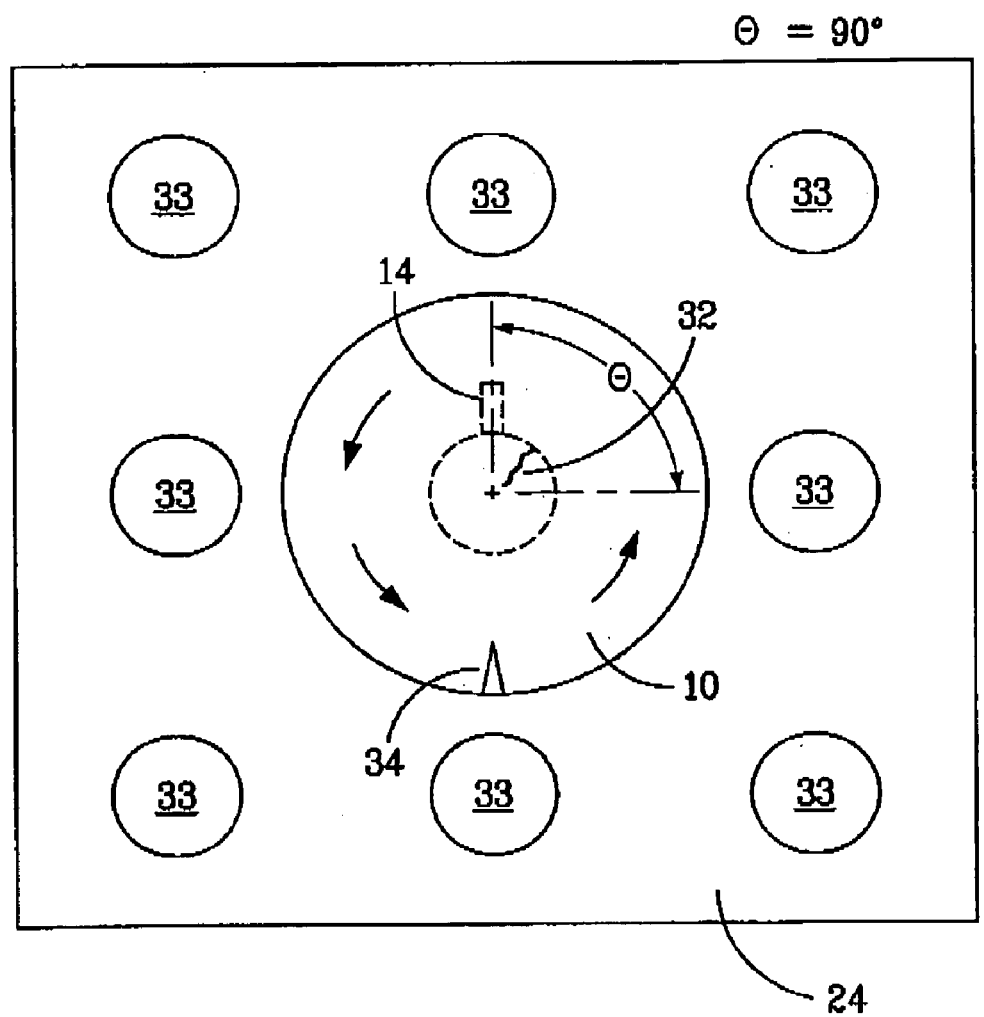
FIG. 4C shows a schematic top side view of a rotating concave eddy current probe placed on top of raised head fastener, with 90 degree circumferential (θ) rotation, according to the present invention.

FIG. 4B shows the EC probe 10 rotated to θ=45 degrees, where the test coil 14 now lines up with crack 32. FIG. 4C shows the EC probe 10 rotated to θ=90 degree. For a complete inspection of the rivet, probe 10 would be rotated 360 degrees completely around one revolution. During inspection, the probe's circumferential angle changes from 0 to 360 degrees, and perturbations in the impedance plane plot indicate the presence of a hidden crack(s) in the structural skin underneath.

Figure 5:
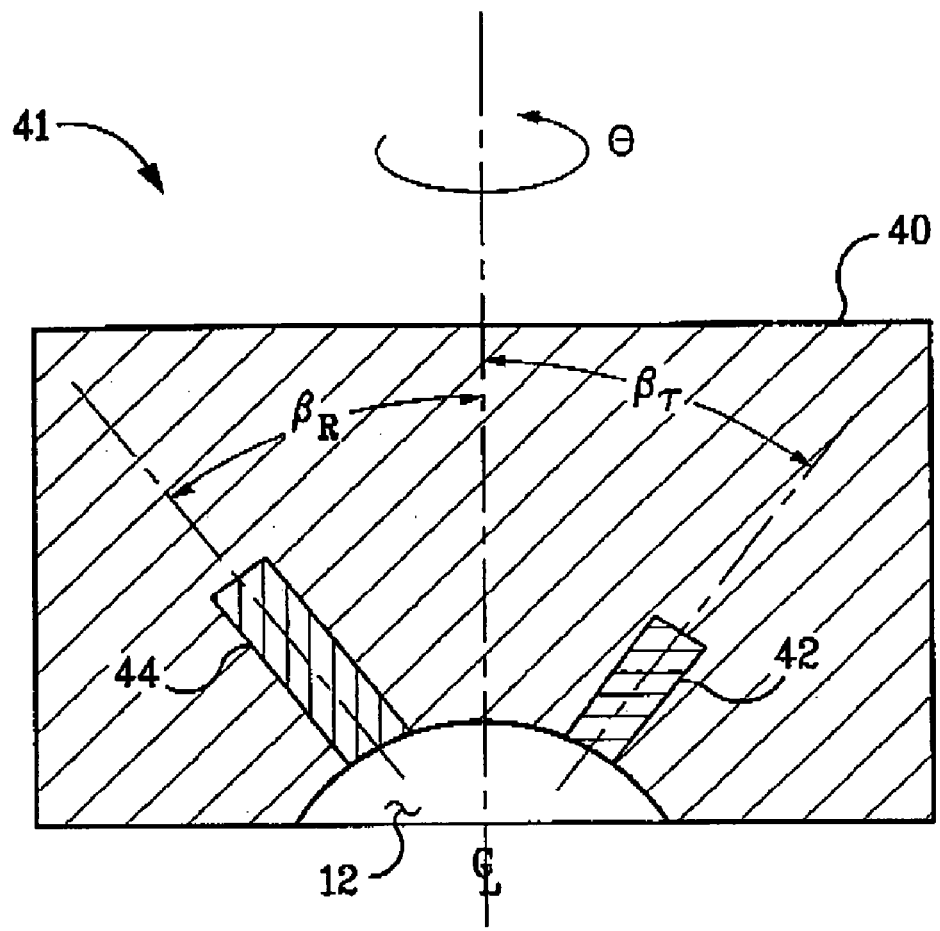
FIG. 5 shows a schematic cross-section side view of the dual-coil type of rotating concave eddy current probe, according to the present invention.

FIG. 5 shows a schematic cross-section side view of another example of a dual-coil type of rotating concave eddy current probe, according to the present invention. Probe 41 has two coils, a transmitter coil 42 and a receiver coil 44, embedded within probe body 40. Transmitter coil 42 is oriented at a first angle, $\beta_T$, with respect to the probe's centerline; and receiver coil 44 is oriented at a second angle, $\beta_R$, with respect to the probe's centerline. The two different coils, 42 and 44, can be located at opposite circumferential positions from each other (e.g., at $\theta$=0 and $\theta$=180 degrees). The transmitter coil's angle $\beta_T$, can be the same, or different, from the receiver coil's angle $\beta_R$. The size of the magnetic coils (i.e., diameter and length, number of turns, etc.) can be the same for both coils 42 and 44, or different. Receiver coil 44 picks up the magnetic field generated by the eddy currents induced by transmitter coil 42, as is well-known in the art. A second electrical connector (not shown) would be used in body 40.

Figure 6:
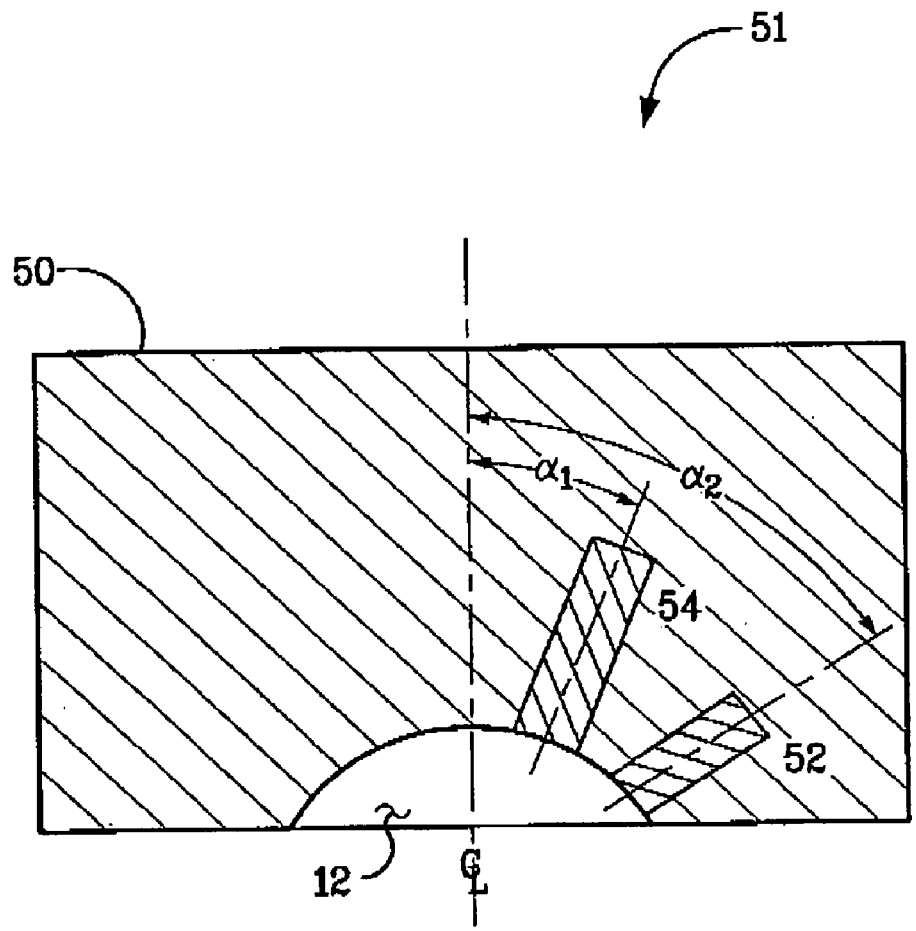
FIG. 6 shows a schematic cross-section side view of another example of a rotating concave eddy current probe, according to the present invention.

FIG. 6 shows a schematic cross-section side view of another example of a dual-coil type of rotating concave eddy current probe, according to the present invention. Probe 51 has two coils, a transmitter coil 52 and a receiver coil 54, embedded within probe body 50. Transmitter coil 52 is oriented at a first angle, $\alpha_T$, with respect to the probe's centerline; and receiver coil 52 is oriented at a second angle, $\alpha_R$, with respect to the probe's centerline. The two different coils, 52 and 54, can be located at the same circumferential positions within body 50, but with different orientation angles (i.e., $\alpha_T$ is not equal to $\alpha_R$).

Figure 7:
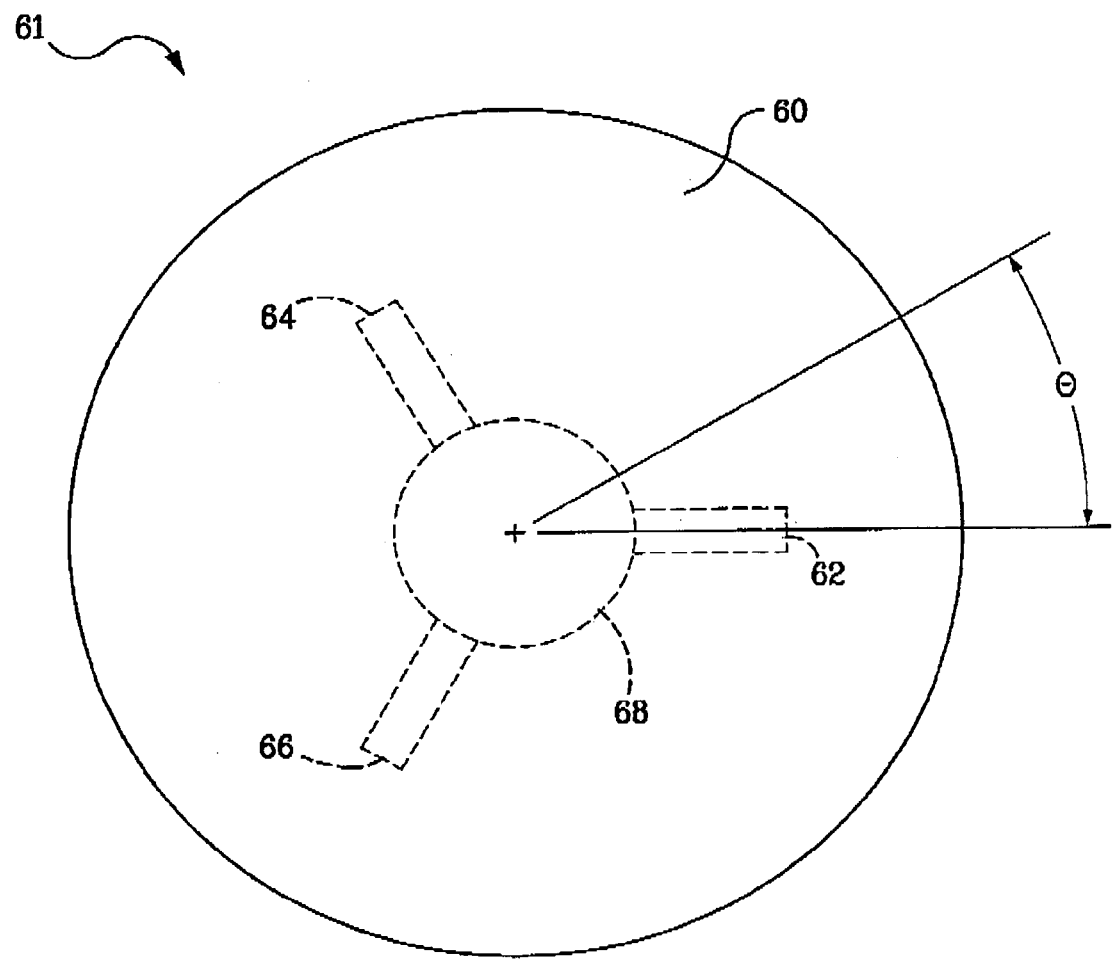
FIG. 7 shows a schematic top side view of the multi-coil type of the rotating concave eddy current probe, according to the present invention.

FIG. 7 shows a schematic top view of an example of a three-coil type of rotating concave eddy current probe, according to the present invention. Probe 61 has three coils, 62, 64, and 66, embedded within probe body 60, at 120 degrees circumferentially-apart from each other.

Figure 8:
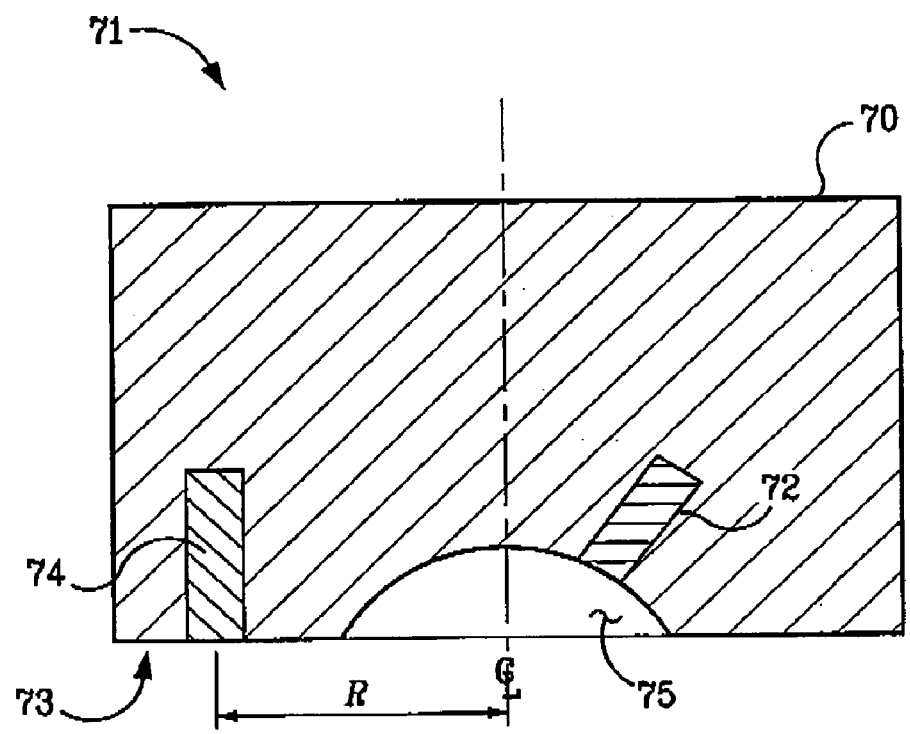
FIG. 8 shows a schematic top view of another variation on the multi-coil type of the rotating concave eddy current probe, according to the present invention.

FIG. 8 shows a schematic cross-section side view of another example of a rotating concave eddy current probe, according to the present invention. Probe 71 has two different test coils, 72 and 74, embedded within probe body 70. First test coil 72 is as described previously. The second test coil, 74, is oriented so that the coil's axis is perpendicular to the bottom surface 73 of body 70 (i.e., vertically), and is located at a radial position, R, outside of concave dimple 75, close to the outer diameter of body 70. The two different test coils, 72 and 74, can be located circumferentially at the same circumferential angle, or at different angles (e.g., at $\theta$=0 and $\theta$=180 degrees, as illustrated in FIG. 8). The outside (second) coil 74 is more sensitive to cracks located outside of the rivet's head, while the inside (first) coil 72 is more sensitive to cracks located underneath the rivet's head.

Figure 9:
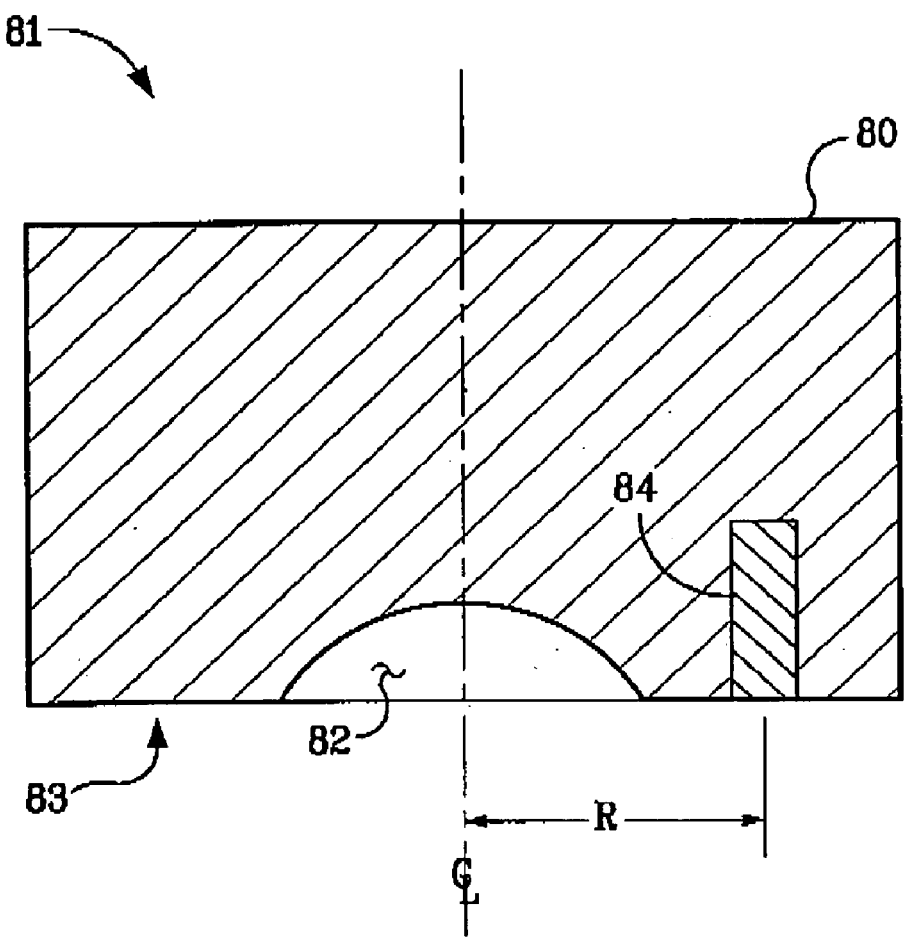
FIG. 9 shows a schematic cross-section side view of another example of a rotating concave eddy current probe, according to the present invention.

FIG. 9 shows a schematic cross-section side view of another example of a rotating concave eddy current probe, according to the present invention. Test coils 84 is embedded within probe body 80. Coil 84 is oriented so that the coil's axis is perpendicular to the bottom surface 83 of body 80 (i.e., vertically), and is located at a radial position, R, outside of concave dimple 82, close to the outer diameter of body 80.

Figure 10:
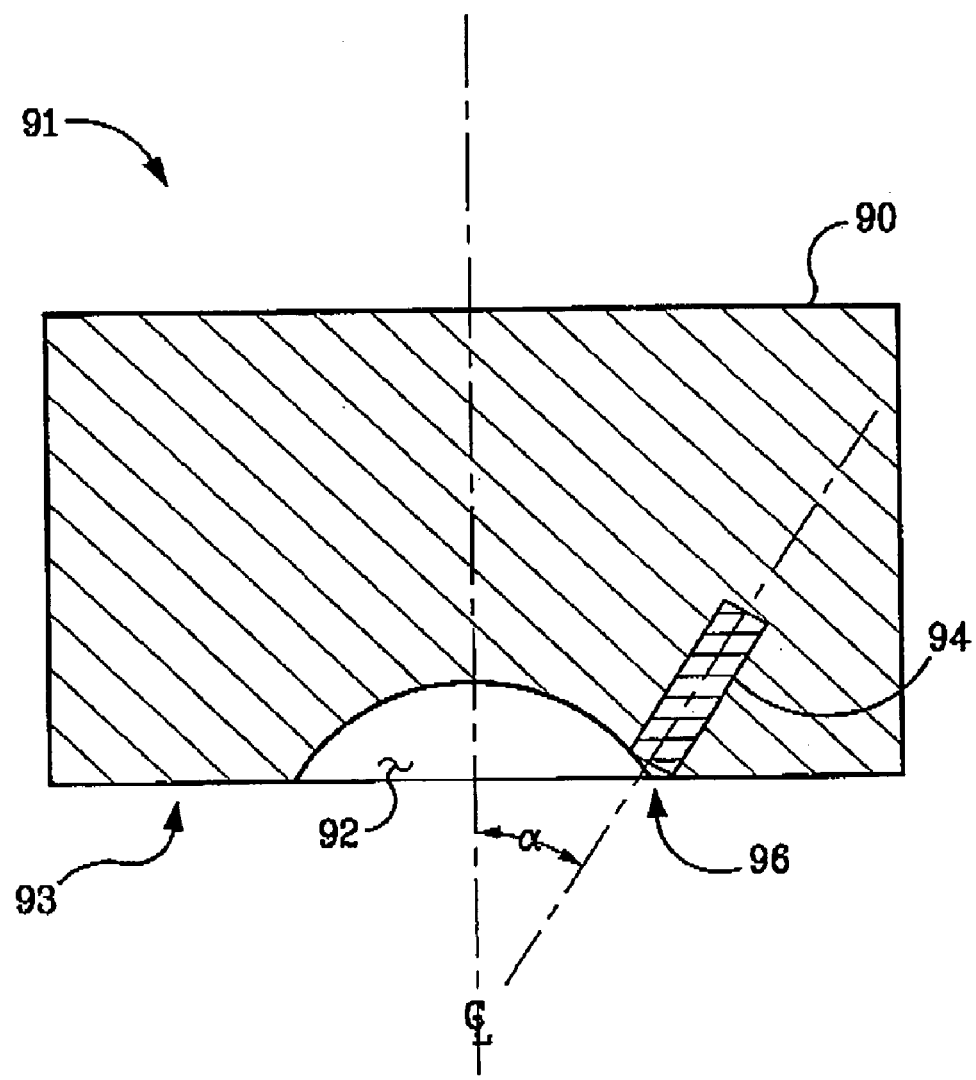
FIG. 10 shows a schematic cross-section side view of another example of a rotating concave eddy current probe, according to the present invention.

FIG. 10 shows a schematic cross-section side view of another example of a rotating concave eddy current probe, according to the present invention. Probe 91 has a test coil 94 embedded within probe body 90. Coil 94 is oriented so that the coil's axis passes through the intersection point 96, which is located at the intersection of the outermost diameter of concave dimple 92 and the bottom surface 93 of housing 90. The orientation of the coil's axis is neither perpendicular to the surface of concave dimple 92, nor is it perpendicular to the bottom surface 93, but, rather, somewhere in-between. As shown in FIG. 10, the angle of orientation, $\alpha$, can be about 20-50 degrees; and, alternatively, can be about 30-40 degrees.

Figure 11:
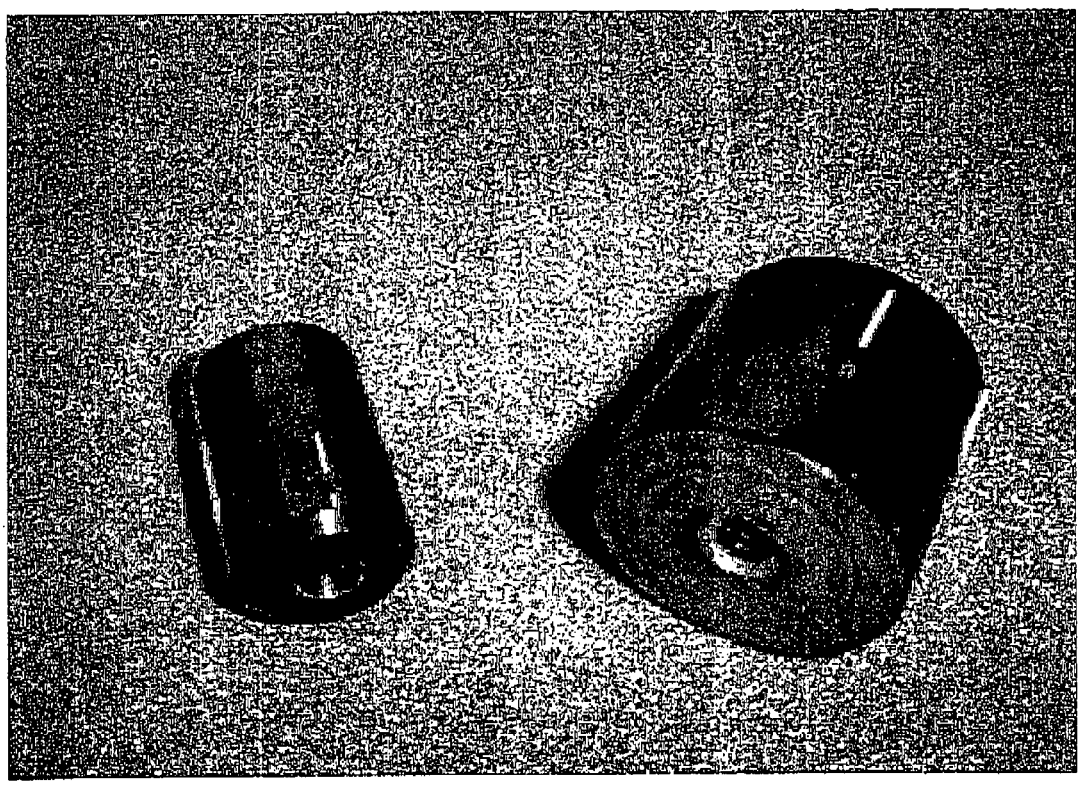
FIG. 11 shows a photograph of a pair of concave EC probes, according to the present invention.
Figure 12:
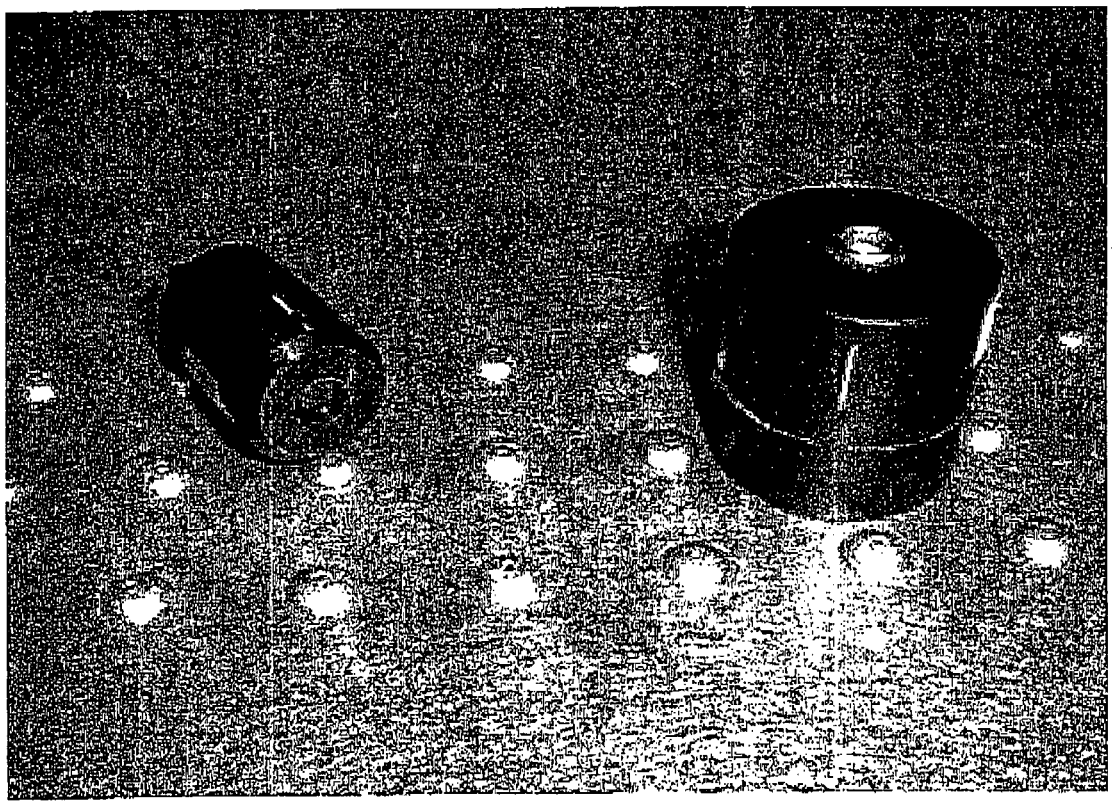
FIG. 12 shows another photograph of a pair of concave EC probes, according to the present invention.

FIGS. 11 and 12 show photographs of a pair of different sized concave EC probes, according to the present invention. The probe's body is made of Delrin plastic. In one of the probes, the bottom edges have been chamfered. FIG. 12 shows how the probe is placed on top of an aluminum rivet in a grid of rivets holding together two aluminum structural skins.

Figures 13A, 13B, 13C:
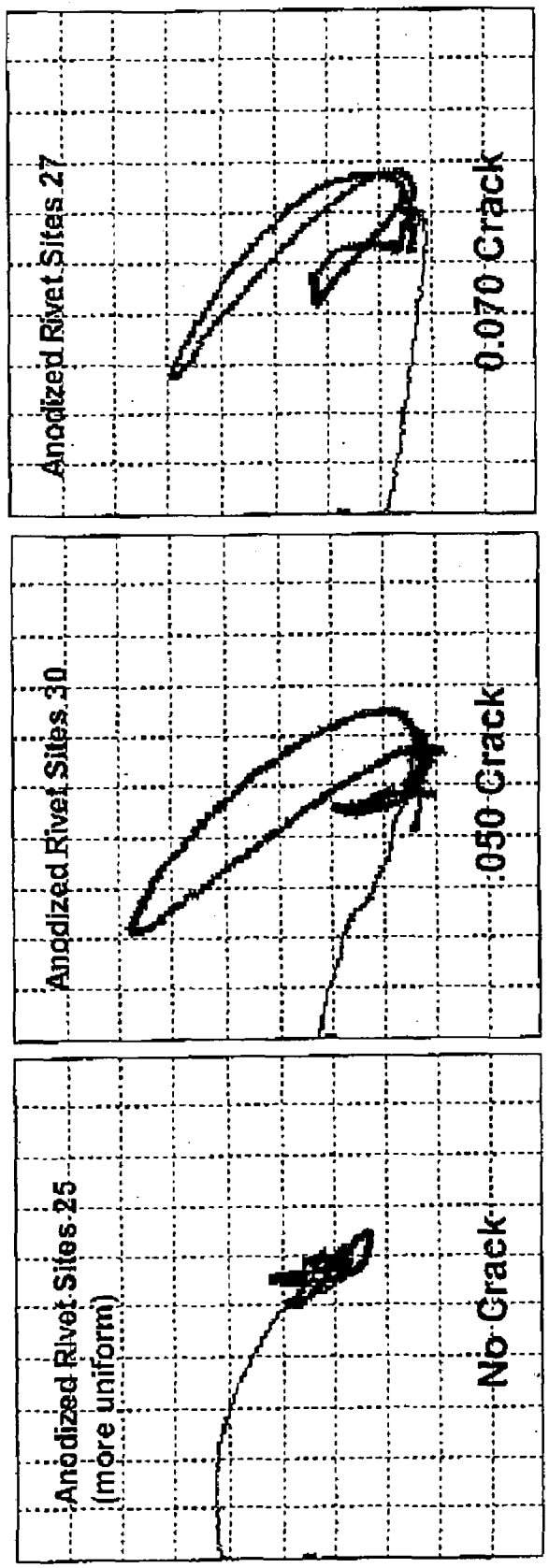
FIGS. 13A, 13B, and 13C show examples of impendence plane plots for crack detection in high conductivity rivet sites using the rotating, concave eddy current probe, according to the present invention.

FIGS. 13A, 13B, and 13C show examples of impendence plane plots for crack detection in high conductivity rivet sites using the rotating, concave eddy current probe, according to the present invention. In these plots, the horizontal (X) axis represents the amplitude, and the vertical axis (Y) represents the phase of the impendence signal of the probe. These experimental results illustrate successful detection of hidden fatigue cracks in the structural skin that are 0.050 inches long (FIG. 12B) and 0.070 inches long (FIG. 12C), as compared to the baseline case of no cracks (FIG. 12A).

The particular examples discussed above are cited to illustrate particular embodiments of the invention. Other applications and embodiments of the apparatus and method of the present invention will become evident to those skilled in the art. It is to be understood that the invention is not limited in its application to the details of construction, materials used, and the arrangements of components set forth in the following description or illustrated in the drawings.

The scope of the invention is defined by the claims appended hereto.

What is claimed is:

1. A rotating concave eddy current probe, comprising:
   a probe body comprising a right circular-cylinder made of a non-conducting material; the body having a central axis, an upper surface, a bottom surface, and a cylindrically-shaped side surface;
   a concave dimple recessed into the bottom surface of the probe body, centered on the cylinder's central axis, and having an axisymmetric inner surface that conforms closely to the shape of a head of a raised head fastener;
   a magnetic test coil embedded within the probe body; comprising a right circular-cylinder with a lower end, an upper end, and a central axis;
   a pair of electrical leads embedded inside the body, for supplying electrical current to the coil through the coil's upper end; and
   electrical connection means disposed on the exterior of the probe body, and connected to the pair of embedded electrical leads, for connecting the magnetic test coil with a source of electrical current;
   wherein the lower end of the test coil is located flush with the inner surface of the concave dimple;
   wherein the central axis of the test coil is aligned to intersect the central axis of the probe body; and
   wherein the central axis of the test coil is oriented at an inclined angle, $\alpha$, relative to the probe body's central axis, that aligns the test coil's axis to be perpendicular to the concave surface of the recessed dimple.

2. The eddy current probe of claim 1, wherein the inclined angle, $\alpha$, ranges from 20-60 degrees.

3. The eddy current probe of claim 1, wherein the inclined angle, $\alpha$, ranges from 30-50 degrees.

4. The eddy current probe of claim 1, wherein the inclined angle, $\alpha$, ranges from 40-50 degrees.

5. The eddy current probe of claim 1, wherein the probe body has chamfered corners at the bottom surface.

6. The eddy current probe of claim 1, wherein the outside diameter of the probe body is at least twice as large as the outside diameter of the concave recessed dimple.

7. The eddy current probe of claim 1, wherein the electrical connection means comprises a coaxial electrical socket located on the upper surface of the probe body, aligned with the probe body's central axis.

8. The eddy current probe of claim 1, wherein the non-conducting materials comprises a plastic or ceramic material.

9. The eddy current probe of claim 1, additionally comprising a second magnetic coil embedded with the probe body, wherein the central axis of the second coil is oriented perpendicular to the bottom surface of the probe body, and is located at a radial position that is greater than the diameter of the recessed concave dimple.

10. The eddy current probe of claim 1, wherein the raised head fastener is a buttonhead-type rivet.

11. A method of inspecting for one or more cracks located underneath a head of a raised head fastener, comprising:
   a) placing a rotating eddy current probe according to claim 1 over the head of the raised head fastener;
   b) energizing the probe;
   c) rotating the probe circumferentially around the fastener's central axis; while measuring the impedance of the probe; and
   d) making impedance plane plots corresponding to multiple circumferential positions of the probe; and
   e) inspecting the impedance plane plots for any perturbations in the probe's response that indicate the presence of a crack located underneath the raised head.

12. A rotating concave eddy current probe, comprising:
   a probe body comprising a right circular-cylinder made of a non-conducting material; the body having a central axis, an upper surface, a bottom surface, and a cylindrically-shaped side surface;
   a concave dimple recessed into the bottom surface of the probe body, centered on the cylinder's central axis, and having an axisymmetric inner surface that conforms closely to the shape of a head of a raised head fastener;
   a first and a second magnetic coil, both embedded within the probe body; each coil comprising a right circular-cylinder with a lower end, an upper end, a central axis, and a pair of electrical leads embedded inside the body, for supplying electrical current to the coil through the coil's upper end;
   wherein the lower ends of each coil are located flush with the inner surface of the concave dimple;
   wherein the central axis of each coil is aligned to intersect the central axis of the probe body; and
   wherein the central axis of each coil is aligned to be perpendicular to the concave surface of the recessed dimple; and
   wherein the central axis of the first coil is oriented at a first inclined angle, $\alpha_1$, relative to the probe body's central axis, and the central axis of the second coil is oriented at a second inclined angle, $\alpha_2$, relative to the probe body's central axis.

13. The eddy current probe of claim 12, wherein the first inclined angle, $\alpha_1$, is equal to the second inclined angle, $\alpha_2$.

14. The eddy current probe of claim 13, wherein the first inclined angle, $\alpha_1$, is equal to the second inclined angle, $\alpha_2$.

15. The eddy current probe of claim 12, wherein the first inclined angle, $\alpha_1$, is different than the second inclined angle, $\alpha_2$.

16. The eddy current probe of claim 15, wherein the first magnetic coil is located at the same circumferential position as the second magnetic coil.

17. The eddy current probe of claim 12, wherein the first magnetic coil has a different size than the second magnetic coil.

18. The eddy current probe of claim 12, wherein the first magnetic coil is a transmitter coil and the second magnetic coil is a receiver coil.

19. The eddy current probe of claim 18, wherein the second magnetic coil is located at a circumferential position that is 180 degrees opposite from the first magnetic coil.

20. The eddy current probe of claim 12, wherein the raised head fastener is a buttonhead-type rivet.

* * * * *